(12) United States Patent
Takubo et al.

(10) Patent No.: US 11,878,079 B2
(45) Date of Patent: *Jan. 23, 2024

(54) PULLULAN CAPSULES

(71) Applicant: Capsugel Belgium NV, Bornem (BE)

(72) Inventors: Takahisa Takubo, Kanagawa (JP); Claire Geneviève Odile Tardy, Urschenheim (FR)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/145,463

(22) Filed: Dec. 22, 2022

(65) Prior Publication Data
US 2023/0131084 A1   Apr. 27, 2023

Related U.S. Application Data

(63) Continuation of application No. 16/604,540, filed as application No. PCT/IB2018/000448 on Apr. 10, 2018, now Pat. No. 11,576,870.

(60) Provisional application No. 62/485,854, filed on Apr. 14, 2017.

(51) Int. Cl.
*A61K 9/48* (2006.01)
*A61K 47/36* (2006.01)

(52) U.S. Cl.
CPC ............ *A61K 9/4816* (2013.01); *A61K 47/36* (2013.01)

(58) Field of Classification Search
None
See application file for complete search history.

(56) References Cited

U.S. PATENT DOCUMENTS

| | | |
|---|---|---|
| 3,654,088 A | 4/1972 | Coker et al. |
| 3,779,972 A | 12/1973 | Minieri |
| 3,784,390 A | 1/1974 | Hljiya et al. |
| 3,827,937 A | 8/1974 | Kato et al. |
| 3,870,537 A | 3/1975 | Hijiya et al. |
| 3,871,892 A | 3/1975 | Hijiya et al. |
| 3,872,228 A | 3/1975 | Hijiya et al. |
| 3,873,333 A | 3/1975 | Hijiya et al. |
| 3,875,308 A | 4/1975 | Kato et al. |
| 3,888,809 A | 6/1975 | Nakashio et al. |
| 3,912,591 A | 10/1975 | Kato et al. |
| 3,931,146 A | 1/1976 | Kato et al. |
| 3,932,192 A | 1/1976 | Nakashio et al. |
| 3,936,347 A | 2/1976 | Nomura |
| 3,954,724 A | 5/1976 | Nakashio et al. |
| 3,959,009 A | 5/1976 | Kato et al. |
| 3,960,685 A | 6/1976 | Sano et al. |
| 3,962,155 A | 6/1976 | Usamoto et al. |
| 3,972,997 A | 8/1976 | Nakashio et al. |
| 3,976,605 A | 8/1976 | Matsunaga et al. |
| 3,976,819 A | 8/1976 | Mori et al. |
| 3,992,496 A | 11/1976 | Matsunaga et al. |
| 3,993,840 A | 11/1976 | Tsuji et al. |
| 3,997,703 A | 12/1976 | Nakashio et al. |
| 4,004,977 A | 1/1977 | Kato et al. |
| 4,018,233 A | 4/1977 | Miyake |
| 4,029,616 A | 6/1977 | Nakashio et al. |
| 4,029,886 A | 6/1977 | Nakashio et al. |
| 4,032,403 A | 6/1977 | Sakai et al. |
| 4,045,204 A | 8/1977 | Matsunaga et al. |
| 4,045,388 A | 8/1977 | Matsunaga et al. |
| 4,067,141 A | 1/1978 | Matsunaga et al. |
| 4,152,170 A | 5/1979 | Nagase et al. |
| 4,167,623 A | 9/1979 | Fujita et al. |
| 4,174,440 A | 11/1979 | Fujita et al. |
| 4,186,024 A | 1/1980 | Fujimoto et al. |
| 4,205,218 A | 5/1980 | Fukami et al. |
| 4,247,642 A | 1/1981 | Hirohara et al. |
| 4,306,059 A | 12/1981 | Yokobayashi et al. |
| 4,338,398 A | 7/1982 | Yoneyama |
| 4,370,472 A | 1/1983 | Igarashi et al. |
| 4,372,883 A | 2/1983 | Matuhashi et al. |
| 4,474,756 A | 10/1984 | Mitsuhashi et al. |
| 4,562,020 A | 12/1985 | Hijiya et al. |
| 4,579,259 A | 4/1986 | Hirao et al. |
| 4,610,891 A | 9/1986 | Miyamoto et al. |
| 4,618,664 A | 10/1986 | Ohnishi |
| 4,628,028 A | 12/1986 | Katkocin et al. |
| 4,650,757 A | 3/1987 | David et al. |
| 4,659,569 A | 4/1987 | Mitsuhashi et al. |
| 4,683,298 A | 7/1987 | Yalpani |
| 4,745,042 A | 5/1988 | Sasago et al. |
| 4,758,660 A | 7/1988 | Takeuchi et al. |
| 4,777,065 A | 10/1988 | Hirao et al. |

(Continued)

FOREIGN PATENT DOCUMENTS

| | | |
|---|---|---|
| AU | 2018251256 A1 | 11/2019 |
| AU | 2018253392 A1 | 11/2019 |

(Continued)

OTHER PUBLICATIONS

Bouvens, H.O. et al., "Polysaccharides elaborated by Pullularia pullulans; Part I. The neutral glucan synthesized from sucrose solutions," *Acta Chemica Scandinavica*, 16(3):615-622 (1962).

Cade et al., "Liquid Filling in Hard Gelatin Capsules—Preliminary Steps," *Bulletin Technique Gattefosse*, 89:15-19 (1996).

European Patent Office Communication dated May 2, 2014, from EPC Patent Application No. 12705407.0 (6 pages).

International Search Report for PCT/IB2012/000176 (dated Aug. 7, 2012).

International Search Report and Written Opinion for PCT/IB2018/000448 (dated Jul. 17, 2018).

(Continued)

*Primary Examiner* — Melissa S Mercier
(74) *Attorney, Agent, or Firm* — Klarquist Sparkman, LLP

(57) ABSTRACT

The instant disclosure provides a capsule composition comprising pullulan, a setting system and a surfactant system that is a sucroglyceride or a sugar fatty acid ester, and methods for making such capsules.

18 Claims, 2 Drawing Sheets

(56) References Cited

U.S. PATENT DOCUMENTS

| | | | |
|---|---|---|---|
| 4,816,445 A | 3/1989 | Mitsuhashi et al. | |
| 4,822,601 A | 4/1989 | Goode et al. | |
| 4,824,938 A | 4/1989 | Koyama et al. | |
| 4,889,728 A | 12/1989 | Maeda et al. | |
| 4,927,636 A | 5/1990 | Hijiya et al. | |
| 4,962,026 A | 10/1990 | Keng | |
| 4,965,347 A | 10/1990 | Misaki et al. | |
| 5,019,514 A | 5/1991 | Bock et al. | |
| 5,073,628 A | 12/1991 | Matsuhashi et al. | |
| 5,077,336 A | 12/1991 | Nakashita et al. | |
| 5,082,803 A | 1/1992 | Sumita | |
| 5,100,877 A | 3/1992 | Mori et al. | |
| 5,143,646 A | 9/1992 | Nochumson et al. | |
| 5,147,795 A | 9/1992 | Ara et al. | |
| 5,147,796 A | 9/1992 | Ara et al. | |
| 5,264,223 A | 11/1993 | Yamamoto et al. | |
| 5,268,460 A | 12/1993 | Thorne et al. | |
| 5,281,527 A | 1/1994 | Tachibana et al. | |
| 5,316,691 A | 5/1994 | Sone et al. | |
| 5,362,779 A | 11/1994 | Kitayama et al. | |
| 5,366,879 A | 11/1994 | Kitahata et al. | |
| 5,411,945 A | 5/1995 | Ozaki et al. | |
| 5,518,902 A | 5/1996 | Ozaki et al. | |
| 5,552,166 A | 9/1996 | Harada et al. | |
| 5,583,039 A | 12/1996 | Park et al. | |
| 5,583,244 A | 12/1996 | Uchida et al. | |
| 5,631,221 A | 5/1997 | Kohno et al. | |
| 5,709,801 A | 1/1998 | Murofushi et al. | |
| 5,756,123 A | 5/1998 | Yamamoto et al. | |
| 5,837,673 A | 11/1998 | Tsujihara et al. | |
| 5,871,088 A | 2/1999 | Tanabe | |
| 5,874,401 A | 2/1999 | Sanou et al. | |
| 6,242,224 B1 | 6/2001 | Nakano et al. | |
| 6,368,635 B1 | 4/2002 | Akiyama et al. | |
| 6,387,666 B1 | 5/2002 | Thorne et al. | |
| 6,449,925 B1 | 9/2002 | Otsu et al. | |
| 6,596,298 B2 | 7/2003 | Leung et al. | |
| 6,610,810 B2 | 8/2003 | Phillips et al. | |
| 6,887,307 B1 * | 5/2005 | Scott | C08J 5/18 424/463 |
| 6,916,796 B2 | 7/2005 | Wolf | |
| 6,972,189 B2 | 12/2005 | Han et al. | |
| 7,098,013 B2 | 8/2006 | Kubota et al. | |
| 7,101,533 B2 | 9/2006 | Matsuo et al. | |
| 7,179,891 B2 | 2/2007 | Mayumi et al. | |
| 7,186,824 B2 | 3/2007 | Aga et al. | |
| 7,259,197 B2 | 8/2007 | Mitsui et al. | |
| 7,265,168 B2 | 9/2007 | Mitsui et al. | |
| 7,265,191 B2 | 9/2007 | Kinoshita et al. | |
| 7,267,718 B2 | 9/2007 | Scott et al. | |
| 7,396,543 B2 | 7/2008 | Matsunaga et al. | |
| 7,414,038 B2 | 8/2008 | Kinugasa et al. | |
| 7,417,135 B2 | 8/2008 | Bardowski et al. | |
| 7,445,921 B2 | 11/2008 | Oura et al. | |
| 7,638,241 B2 | 12/2009 | Lee et al. | |
| 7,749,538 B2 | 7/2010 | Sugimoto et al. | |
| 7,815,935 B2 | 10/2010 | Li et al. | |
| 7,815,952 B2 | 10/2010 | Inoue et al. | |
| 7,856,989 B2 | 12/2010 | Karles et al. | |
| 8,017,143 B2 | 9/2011 | Shin et al. | |
| 8,105,625 B2 * | 1/2012 | Rajewski | A61K 9/0056 424/452 |
| 8,168,778 B2 | 5/2012 | Nishimoto et al. | |
| 8,192,761 B2 | 6/2012 | Ochiai et al. | |
| 8,324,375 B2 | 12/2012 | Watanabe et al. | |
| 8,361,386 B2 | 1/2013 | Davis et al. | |
| 8,536,111 B2 | 9/2013 | Watanabe et al. | |
| 8,632,652 B2 | 1/2014 | Lee et al. | |
| 8,791,232 B2 | 7/2014 | Derkx et al. | |
| 8,821,934 B2 | 9/2014 | Sugimoto et al. | |
| 8,900,629 B2 | 12/2014 | Rajewski et al. | |
| 8,951,996 B2 | 2/2015 | Giliyar et al. | |
| 8,986,735 B2 | 3/2015 | Schobel et al. | |
| 9,073,294 B2 | 7/2015 | Kumar et al. | |
| 11,576,870 B2 * | 2/2023 | Takubo | A61K 47/36 |
| 2002/0009522 A1 | 1/2002 | Hirai et al. | |
| 2002/0131990 A1 | 9/2002 | Barkalow et al. | |
| 2003/0017209 A1 | 1/2003 | Parikh et al. | |
| 2003/0054499 A1 | 3/2003 | Han et al. | |
| 2003/0059479 A1 | 3/2003 | Miyake | |
| 2003/0087002 A1 | 5/2003 | Fouache et al. | |
| 2003/0104048 A1 | 6/2003 | Patel | |
| 2003/0108593 A1 | 6/2003 | Oku et al. | |
| 2003/0134409 A1 | 7/2003 | Mallouk et al. | |
| 2004/0013723 A1 | 1/2004 | Parikh et al. | |
| 2004/0126330 A1 | 7/2004 | Awamura et al. | |
| 2004/0131661 A1 | 7/2004 | Auffret et al. | |
| 2004/0236017 A1 | 11/2004 | Bruzzano et al. | |
| 2005/0019448 A1 | 1/2005 | Engelhardt | |
| 2005/0031853 A1 | 2/2005 | Scott et al. | |
| 2005/0065030 A1 | 3/2005 | Oku et al. | |
| 2005/0202083 A1 | 9/2005 | Kumar et al. | |
| 2005/0249676 A1 | 11/2005 | Scott et al. | |
| 2006/0011118 A1 | 1/2006 | Hayashi et al. | |
| 2006/0147542 A1 | 7/2006 | Ono et al. | |
| 2006/0159752 A1 | 7/2006 | Jain et al. | |
| 2006/0223140 A1 | 10/2006 | Oura et al. | |
| 2006/0233875 A1 | 10/2006 | Mathur et al. | |
| 2006/0257482 A1 | 11/2006 | Kumar et al. | |
| 2007/0042035 A1 | 2/2007 | Momoi | |
| 2007/0042970 A1 | 2/2007 | Sunamoto et al. | |
| 2007/0087939 A1 | 4/2007 | Cade | |
| 2007/0092600 A1 | 4/2007 | Miyai et al. | |
| 2007/0099996 A1 | 5/2007 | Isloor | |
| 2007/0218189 A1 | 9/2007 | Oku et al. | |
| 2007/0219250 A1 | 9/2007 | Singh et al. | |
| 2007/0258941 A1 | 11/2007 | Pfister | |
| 2007/0292481 A1 | 12/2007 | Hoffman et al. | |
| 2008/0008750 A1 | 1/2008 | Tochio et al. | |
| 2008/0038432 A1 | 2/2008 | Hoffman et al. | |
| 2008/0223395 A1 | 9/2008 | Maillefer et al. | |
| 2008/0248102 A1 | 10/2008 | Rajewski et al. | |
| 2008/0274187 A1 | 11/2008 | Cao | |
| 2009/0048188 A1 | 2/2009 | Matsuo et al. | |
| 2009/0110728 A1 | 4/2009 | Rastogi et al. | |
| 2009/0274636 A1 | 11/2009 | Shinohara et al. | |
| 2009/0291138 A1 | 11/2009 | Watanabe et al. | |
| 2010/0003590 A1 | 1/2010 | Park et al. | |
| 2010/0093875 A1 | 4/2010 | Matsui et al. | |
| 2010/0166690 A1 | 7/2010 | Masachika | |
| 2011/0015309 A1 | 1/2011 | Brocker et al. | |
| 2011/0020757 A1 | 1/2011 | Kawauchi et al. | |
| 2011/0086070 A1 | 4/2011 | Talwar et al. | |
| 2011/0091814 A1 | 4/2011 | Endo | |
| 2011/0139164 A1 | 6/2011 | Mua et al. | |
| 2011/0177137 A1 | 7/2011 | Chauhan et al. | |
| 2011/0177297 A1 | 7/2011 | Jung et al. | |
| 2011/0206729 A1 | 8/2011 | Akiyoshi et al. | |
| 2011/0207686 A1 | 8/2011 | Lecommandoux et al. | |
| 2011/0236935 A1 | 9/2011 | Mikkelsen et al. | |
| 2011/0244047 A1 | 10/2011 | Asari et al. | |
| 2011/0268797 A1 | 11/2011 | Cifter et al. | |
| 2011/0292566 A1 | 12/2011 | Tan et al. | |
| 2012/0037039 A1 | 2/2012 | Nieto | |
| 2013/0005831 A1 | 1/2013 | Rajewski et al. | |
| 2013/0160779 A1 | 6/2013 | Chida et al. | |
| 2013/0195941 A1 | 8/2013 | Shibuya et al. | |
| 2013/0244082 A1 | 9/2013 | Lee et al. | |
| 2013/0287842 A1 | 10/2013 | Cade et al. | |
| 2013/0288932 A1 | 10/2013 | Mackenzie et al. | |
| 2013/0323307 A1 | 12/2013 | Jeon et al. | |
| 2013/0344147 A1 | 12/2013 | Kainose et al. | |
| 2014/0010882 A1 | 1/2014 | Matsuda et al. | |
| 2014/0170213 A1 | 6/2014 | Kim et al. | |
| 2014/0178555 A1 | 6/2014 | Fujimoto et al. | |
| 2014/0187538 A1 | 7/2014 | Bogo et al. | |
| 2015/0111862 A1 | 4/2015 | Podolski et al. | |
| 2015/0112250 A1 | 4/2015 | Kwon | |
| 2015/0209275 A1 | 7/2015 | Choonara et al. | |
| 2015/0274605 A1 | 10/2015 | Waldron et al. | |
| 2016/0038729 A1 | 2/2016 | Kato | |
| 2018/0256506 A1 | 9/2018 | Cade et al. | |

(56) References Cited

U.S. PATENT DOCUMENTS

2019/0046454 A1 2/2019 Cade et al.
2020/0291439 A1 9/2020 Breit et al.

FOREIGN PATENT DOCUMENTS

| | | |
|---|---|---|
| BR | 112019021396 A2 | 4/2020 |
| BR | 112019021391 A2 | 5/2020 |
| CA | 1037887 A | 9/1978 |
| CA | 2520986 A1 | 4/2000 |
| CA | 3059527 A1 | 10/2018 |
| CA | 3059529 A1 | 10/2018 |
| CN | 1216780 A | 5/1999 |
| CN | 1216781 A | 5/1999 |
| CN | 1106448 C | 4/2003 |
| CN | 1449741 A | 10/2003 |
| CN | 1584596 A | 2/2005 |
| CN | 1602716 A | 4/2005 |
| CN | 1609188 A | 4/2005 |
| CN | 1644675 A | 7/2005 |
| CN | 1289532 C | 8/2005 |
| CN | 1313498 C | 8/2005 |
| CN | 1651467 A | 8/2005 |
| CN | 1651468 A | 8/2005 |
| CN | 1654482 A | 8/2005 |
| CN | 1680571 A | 10/2005 |
| CN | 1696302 A | 11/2005 |
| CN | 1723904 A | 1/2006 |
| CN | 1768860 A | 5/2006 |
| CN | 1264976 C | 7/2006 |
| CN | 1948347 A | 4/2007 |
| CN | 1315873 C | 5/2007 |
| CN | 101036788 A | 9/2007 |
| CN | 101069677 A | 11/2007 |
| CN | 101088879 A | 12/2007 |
| CN | 101100687 A | 1/2008 |
| CN | 101215592 A | 7/2008 |
| CN | 101229379 A | 7/2008 |
| CN | 101254309 A | 9/2008 |
| CN | 101279096 A | 10/2008 |
| CN | 101283774 B | 10/2008 |
| CN | 101416930 B | 4/2009 |
| CN | 101487034 A | 7/2009 |
| CN | 101555507 A | 10/2009 |
| CN | 101560528 A | 10/2009 |
| CN | 100571781 C | 12/2009 |
| CN | 101653171 A | 2/2010 |
| CN | 101669670 A | 3/2010 |
| CN | 101096236 A | 5/2010 |
| CN | 101731410 A | 6/2010 |
| CN | 101755991 A | 6/2010 |
| CN | 101760456 A | 6/2010 |
| CN | 101831000 A | 9/2010 |
| CN | 101836678 A | 9/2010 |
| CN | 101839849 A | 9/2010 |
| CN | 101942493 A | 1/2011 |
| CN | 101988036 A | 3/2011 |
| CN | 102010513 A | 4/2011 |
| CN | 102010526 A | 4/2011 |
| CN | 102027999 A | 4/2011 |
| CN | 102145173 A | 8/2011 |
| CN | 102258484 A | 11/2011 |
| CN | 101974543 A | 5/2012 |
| CN | 102432921 A | 5/2012 |
| CN | 102492630 A | 6/2012 |
| CN | 101579326 A | 7/2012 |
| CN | 102552721 A | 7/2012 |
| CN | 102626279 A | 8/2012 |
| CN | 102670563 A | 9/2012 |
| CN | 102766219 A | 11/2012 |
| CN | 102875742 A | 1/2013 |
| CN | 103015175 A | 4/2013 |
| CN | 103030978 A | 4/2013 |
| CN | 102499451 A | 5/2013 |
| CN | 102499910 B | 6/2013 |
| CN | 102492740 A | 8/2013 |
| CN | 103243135 A | 8/2013 |
| CN | 102600493 A | 12/2013 |
| CN | 102603912 A | 1/2014 |
| CN | 103503983 A | 1/2014 |
| CN | 103060204 A | 2/2014 |
| CN | 103570842 A | 2/2014 |
| CN | 102531773 A | 3/2014 |
| CN | 103626885 A | 3/2014 |
| CN | 103636743 A | 3/2014 |
| CN | 103642086 A | 3/2014 |
| CN | 102783713 A | 4/2014 |
| CN | 103695476 A | 4/2014 |
| CN | 103695500 A | 4/2014 |
| CN | 103724709 A | 4/2014 |
| CN | 103740785 A | 4/2014 |
| CN | 103798253 A | 5/2014 |
| CN | 103805650 A | 5/2014 |
| CN | 103805651 A | 5/2014 |
| CN | 103806275 A | 5/2014 |
| CN | 103880762 A | 6/2014 |
| CN | 103881927 A | 6/2014 |
| CN | 103882076 A | 6/2014 |
| CN | 102994395 A | 7/2014 |
| CN | 103893107 A | 7/2014 |
| CN | 103088085 A | 8/2014 |
| CN | 103961334 A | 8/2014 |
| CN | 103961335 A | 8/2014 |
| CN | 103993042 A | 8/2014 |
| CN | 103305569 A | 9/2014 |
| CN | 104059560 A | 9/2014 |
| CN | 104082851 A | 10/2014 |
| CN | 103409480 A | 11/2014 |
| CN | 104222265 A | 12/2014 |
| CN | 103172757 A | 1/2015 |
| CN | 103255067 A | 1/2015 |
| CN | 103451108 A | 1/2015 |
| CN | 104256251 A | 1/2015 |
| CN | 103416694 A | 2/2015 |
| CN | 104401075 A | 3/2015 |
| CN | 104403135 A | 3/2015 |
| CN | 104432492 A | 3/2015 |
| CN | 104436204 A | 3/2015 |
| CN | 104448019 A | 3/2015 |
| CN | 104448403 A | 3/2015 |
| CN | 104450827 A | 3/2015 |
| CN | 104473822 A | 4/2015 |
| CN | 104479038 A | 4/2015 |
| CN | 104609992 B | 5/2015 |
| CN | 104611783 A | 5/2015 |
| CN | 104651405 A | 5/2015 |
| CN | 104694404 A | 6/2015 |
| CN | 104711374 A | 6/2015 |
| CN | 104725652 A | 6/2015 |
| CN | 103163128 B | 7/2015 |
| CN | 104762753 A | 7/2015 |
| CN | 104798975 A | 7/2015 |
| CN | 104799145 A | 7/2015 |
| CN | 104824508 A | 8/2015 |
| CN | 104840447 A | 8/2015 |
| CN | 104844810 A | 8/2015 |
| CN | 104857560 A | 8/2015 |
| CN | 104859237 A | 8/2015 |
| CN | 104861178 A | 8/2015 |
| CN | 104861214 A | 8/2015 |
| CN | 104861246 A | 8/2015 |
| CN | 102552191 A | 9/2015 |
| CN | 104906622 A | 9/2015 |
| CN | 104911231 A | 9/2015 |
| CN | 104911232 A | 9/2015 |
| CN | 104927266 A | 9/2015 |
| CN | 102964849 A | 10/2015 |
| CN | 103351629 B | 11/2015 |
| CN | 105028864 A | 11/2015 |
| CN | 105039276 A | 11/2015 |
| CN | 105039281 A | 11/2015 |
| CN | 105055365 A | 11/2015 |
| CN | 105106181 A | 12/2015 |
| CN | 105267060 A | 1/2016 |
| CN | 103789363 A | 2/2016 |

(56) References Cited

FOREIGN PATENT DOCUMENTS

| | | |
|---|---|---|
| CN | 110678170 A | 1/2020 |
| CN | 110678555 A | 1/2020 |
| CS | 200778 B1 | 9/1980 |
| DE | 2504108 A1 | 1/1976 |
| DE | 3147193 A1 | 6/1983 |
| DE | 261609 A1 | 11/1988 |
| EP | 0143603 A2 | 6/1985 |
| EP | 0164933 A2 | 12/1985 |
| EP | 0216221 A2 | 4/1987 |
| EP | 0222302 A2 | 5/1987 |
| EP | 0236124 B1 | 9/1987 |
| EP | 0267788 B1 | 5/1988 |
| EP | 0289138 A2 | 11/1988 |
| EP | 0313993 A1 | 5/1989 |
| EP | 0319372 A1 | 6/1989 |
| EP | 0189461 A1 | 7/1990 |
| EP | 0379378 B1 | 7/1990 |
| EP | 0382355 A2 | 8/1990 |
| EP | 0402092 A2 | 12/1990 |
| EP | 0405283 A2 | 1/1991 |
| EP | 0418835 A1 | 3/1991 |
| EP | 0450627 A2 | 10/1991 |
| EP | 0450767 A1 | 10/1991 |
| EP | 0482576 A1 | 4/1992 |
| EP | 0514008 B1 | 11/1992 |
| EP | 0538049 A1 | 4/1993 |
| EP | 0559450 A2 | 9/1993 |
| EP | 0565106 A1 | 10/1993 |
| EP | 0586034 B1 | 3/1994 |
| EP | 0600730 B1 | 6/1994 |
| EP | 0661294 A1 | 7/1995 |
| EP | 0670368 B1 | 9/1995 |
| EP | 0757049 B1 | 2/1997 |
| EP | 0761692 A2 | 3/1997 |
| EP | 0812919 A1 | 12/1997 |
| EP | 0653931 A1 | 9/1999 |
| EP | 1072633 A1 | 1/2001 |
| EP | 0714656 B1 | 2/2001 |
| EP | 1106347 A1 | 6/2001 |
| EP | 1157691 A1 | 11/2001 |
| EP | 1166745 A1 | 1/2002 |
| EP | 1308505 A2 | 5/2003 |
| EP | 1335020 A1 | 8/2003 |
| EP | 1398346 A1 | 3/2004 |
| EP | 1454918 A1 | 9/2004 |
| EP | 1454950 A1 | 9/2004 |
| EP | 1621211 A1 | 2/2006 |
| EP | 1698239 A1 | 9/2006 |
| EP | 1873254 B1 | 1/2008 |
| EP | 1117736 B1 | 8/2008 |
| EP | 0784688 B1 | 7/2009 |
| EP | 2135883 A1 | 12/2009 |
| EP | 2151500 B1 | 2/2010 |
| EP | 2447269 A2 | 5/2012 |
| EP | 2583982 A1 | 4/2013 |
| EP | 2663294 B1 | 11/2013 |
| EP | 2683830 A1 | 1/2014 |
| EP | 3609476 A1 | 2/2020 |
| EP | 3610028 A1 | 2/2020 |
| FR | 2167986 A1 | 8/1973 |
| FR | 2259905 A1 | 8/1975 |
| FR | 2276007 A1 | 1/1976 |
| FR | 2362888 A1 | 3/1978 |
| FR | 2517326 A1 | 6/1983 |
| FR | 2528060 A1 | 12/1983 |
| FR | 2817264 A1 | 5/2002 |
| GB | 1260418 A | 1/1972 |
| GB | 1443918 A | 7/1976 |
| GB | 1493411 A | 11/1977 |
| GB | 1496017 A | 12/1977 |
| GB | 1502797 A | 3/1978 |
| GB | 1559644 A | 1/1980 |
| GB | 2109391 A | 6/1983 |
| GB | 2173088 A | 10/1986 |
| IN | 0434/DEL/2001 | 9/2008 |
| IN | 2718/BOM/2009 | 2/2012 |
| IN | 1374/DEL/2012 | 5/2014 |
| JP | S4821739 B1 | 6/1973 |
| JP | S497492 A | 1/1974 |
| JP | S4983779 A | 8/1974 |
| JP | S49117688 A | 11/1974 |
| JP | S5019943 A | 3/1975 |
| JP | S50105887 A | 8/1975 |
| JP | S50108357 A | 8/1975 |
| JP | S50123931 A | 9/1975 |
| JP | S50148490 A | 11/1975 |
| JP | S511699 A | 1/1976 |
| JP | S517189 A | 1/1976 |
| JP | S5144163 A | 4/1976 |
| JP | S5152484 A | 5/1976 |
| JP | S52109535 A | 9/1977 |
| JP | S52130993 A | 11/1977 |
| JP | S5326867 A | 3/1978 |
| JP | S5379972 A | 7/1978 |
| JP | S5437888 A | 3/1979 |
| JP | S5437889 A | 3/1979 |
| JP | S55118369 A | 9/1980 |
| JP | S56147801 A | 11/1981 |
| JP | S5894364 A | 6/1983 |
| JP | S59172566 A | 9/1984 |
| JP | S61171405 A | 8/1986 |
| JP | S61263915 A | 11/1986 |
| JP | S6262521 A | 3/1987 |
| JP | S63283593 A | 11/1988 |
| JP | H01197432 A | 8/1989 |
| JP | H0321602 A | 1/1991 |
| JP | H0515368 A | 1/1993 |
| JP | H0525201 A | 2/1993 |
| JP | H0565222 A | 3/1993 |
| JP | H0594667 A | 4/1993 |
| JP | H05111364 A | 5/1993 |
| JP | H05148303 A | 6/1993 |
| JP | H05328988 A | 12/1993 |
| JP | H0665302 A | 3/1994 |
| JP | H06157313 A | 6/1994 |
| JP | H0710901 A | 1/1995 |
| JP | H0725891 A | 1/1995 |
| JP | H0725903 A | 1/1995 |
| JP | H0759585 A | 3/1995 |
| JP | H0790250 A | 4/1995 |
| JP | H0847378 A | 2/1996 |
| JP | H08175983 A | 7/1996 |
| JP | H08205865 A | 8/1996 |
| JP | H093106 A | 1/1997 |
| JP | H10155697 A | 6/1998 |
| JP | H10215892 A | 8/1998 |
| JP | H10229839 A | 9/1998 |
| JP | H1139450 A | 2/1999 |
| JP | H1195405 A | 4/1999 |
| JP | H11240806 A | 9/1999 |
| JP | 2000041583 A | 2/2000 |
| JP | 2000202003 A | 7/2000 |
| JP | 2000294439 A | 10/2000 |
| JP | 2000327699 A | 11/2000 |
| JP | 2000348958 A | 12/2000 |
| JP | 2001048765 A | 2/2001 |
| JP | 2001095514 A | 4/2001 |
| JP | 2001191446 A | 7/2001 |
| JP | 2001250733 A | 9/2001 |
| JP | 2001316237 A | 11/2001 |
| JP | 2002033231 A | 1/2002 |
| JP | 2002045118 A | 2/2002 |
| JP | 2003134971 A | 5/2003 |
| JP | 2003238151 A | 8/2003 |
| JP | 2003265111 A | 9/2003 |
| JP | 2003310295 A | 11/2003 |
| JP | 2003313145 A | 11/2003 |
| JP | 2004097233 A | 4/2004 |
| JP | 2004306534 A | 11/2004 |
| JP | 2005112744 A | 4/2005 |
| JP | 2005137935 A | 6/2005 |
| JP | 2005298644 A | 10/2005 |
| JP | 2005302320 A | 10/2005 |
| JP | 2005341958 A | 12/2005 |

(56) References Cited

FOREIGN PATENT DOCUMENTS

| | | |
|---|---|---|
| JP | 2006026544 A | 2/2006 |
| JP | 2006101714 A | 4/2006 |
| JP | 2006143808 A | 6/2006 |
| JP | 2006247505 A | 9/2006 |
| JP | 2007006978 A | 1/2007 |
| JP | 2007089569 A | 4/2007 |
| JP | 2007238908 A | 9/2007 |
| JP | 2007321003 A | 12/2007 |
| JP | 2007536308 A | 12/2007 |
| JP | 2008011807 A | 1/2008 |
| JP | 2008050542 A | 3/2008 |
| JP | 2008133186 A | 6/2008 |
| JP | 2008162966 A | 7/2008 |
| JP | 2008208092 A | 9/2008 |
| JP | 2008208120 A | 9/2008 |
| JP | 2008266458 A | 11/2008 |
| JP | 2009039064 A | 2/2009 |
| JP | 2009161522 A | 7/2009 |
| JP | 2009185022 A | 8/2009 |
| JP | 2009232818 A | 10/2009 |
| JP | 2009233170 A | 10/2009 |
| JP | 2010051327 A | 3/2010 |
| JP | 2010053122 A | 3/2010 |
| JP | 2010158253 A | 7/2010 |
| JP | 2010523594 A | 7/2010 |
| JP | 2010227042 A | 10/2010 |
| JP | 2011182709 A | 9/2011 |
| JP | 2012015152 A | 1/2012 |
| JP | 2012016309 A | 1/2012 |
| JP | 2012017326 A | 1/2012 |
| JP | 2012062279 A | 3/2012 |
| JP | 2012167273 A | 9/2012 |
| JP | 2013000111 A | 1/2013 |
| JP | 2015048316 A | 3/2015 |
| JP | 2015177783 A | 10/2015 |
| JP | 2020512827 A | 4/2020 |
| JP | 2020516653 A | 6/2020 |
| KR | 19890003762 A | 4/1989 |
| KR | 19940014797 B1 | 7/1994 |
| KR | 19970062047 A | 9/1997 |
| KR | 20010083600 A | 9/2001 |
| KR | 20020066298 A | 8/2002 |
| KR | 100508434 B1 | 8/2005 |
| KR | 100739022 B1 | 7/2007 |
| KR | 20100100496 A | 3/2009 |
| KR | 20090036797 A | 4/2009 |
| KR | 20110037739 A | 4/2011 |
| KR | 20110089044 A | 8/2011 |
| KR | 20120064008 | 6/2012 |
| PL | 164352 B1 | 7/1994 |
| RO | 90437 A2 | 10/1986 |
| RO | 105830 B1 | 12/1992 |
| RO | 116203 B1 | 11/2000 |
| RO | 116212 B1 | 11/2000 |
| RS | 20080223 A | 4/2011 |
| RU | 2034923 C1 | 5/1995 |
| SU | 1559718 A1 | 12/1994 |
| WO | WO98/08399 A1 | 3/1998 |
| WO | WO00/47190 A2 | 8/2000 |
| WO | WO00/54606 A1 | 9/2000 |
| WO | WO01/07507 A1 | 2/2001 |
| WO | WO02/46241 A2 | 6/2002 |
| WO | WO02/072862 A2 | 9/2002 |
| WO | WO03/039522 A1 | 5/2003 |
| WO | WO03/105605 A2 | 12/2003 |
| WO | WO2004/012720 A1 | 2/2004 |
| WO | WO2004/056336 A2 | 7/2004 |
| WO | WO2004/078959 A1 | 9/2004 |
| WO | WO2004/096182 A1 | 11/2004 |
| WO | WO2004/096283 A1 | 11/2004 |
| WO | WO2005/006874 A1 | 1/2005 |
| WO | WO2005/016315 A1 | 2/2005 |
| WO | WO2005/020979 A1 | 3/2005 |
| WO | WO2005/079751 A2 | 9/2005 |
| WO | WO2005/082330 A2 | 9/2005 |
| WO | WO2005/105051 A1 | 11/2005 |
| WO | WO2006/018814 A2 | 2/2006 |
| WO | WO2004/041926 A1 | 3/2006 |
| WO | WO2006/033942 A2 | 3/2006 |
| WO | WO2007/011222 A1 | 1/2007 |
| WO | WO2007/095977 A1 | 8/2007 |
| WO | WO2005/084433 A1 | 1/2008 |
| WO | WO2008/047846 A1 | 4/2008 |
| WO | WO2006/082842 A1 | 8/2008 |
| WO | WO2008/101894 A1 | 8/2008 |
| WO | WO2008/124617 A2 | 10/2008 |
| WO | WO2008/137832 A1 | 11/2008 |
| WO | WO2009/050646 A2 | 4/2009 |
| WO | WO2009/123257 A1 | 10/2009 |
| WO | WO2009/138920 A1 | 11/2009 |
| WO | WO2009/154320 A1 | 12/2009 |
| WO | WO2010/139100 A1 | 12/2010 |
| WO | WO2013/085021 A1 | 6/2013 |
| WO | WO2013/123623 A1 | 8/2013 |
| WO | WO2013/146669 A1 | 10/2013 |
| WO | WO2013/162707 A1 | 10/2013 |
| WO | WO2014/000425 A1 | 1/2014 |
| WO | WO2014/051023 A1 | 4/2014 |
| WO | WO2014/072716 A2 | 5/2014 |
| WO | WO2014/209246 A1 | 12/2014 |
| WO | WO2015/092939 A1 | 6/2015 |
| WO | WO2015/133439 A1 | 9/2015 |
| WO | WO2018/189584 A1 | 10/2018 |
| WO | WO2018/189587 A1 | 10/2018 |

OTHER PUBLICATIONS

International Search Report and Written Opinion for PCT/IB2018/000457 (dated Sep. 10, 2018).

Madi, N. et al., "Effect of exogenous calcium on morphological development and biopolymer synthesis in the fungus *Aureobasidium pullulans*," *Enzyme and Microbial Technology*, 21(2):102-107 (Aug. 1, 1997).

Millender, "Capsule Shell Composition and Manufacturing," in *Multiparticulate Oral Drug Delivery. Drugs and the Pharmaceutical Sciences*, 65:357-383, New York, New York, USA: Marcel Dekker, Inc., 1994.

Morris, "Quantitative determination of carbohydrates with Dreywood's anthrone reagent," *Science*, 107:254-255 (Mar. 1948).

Notice of Reasons for Rejection dated May 12, 2015, from related Japanese Patent Application No. 2013-548905, with English-language translation (9 pages).

Office Action for European Application No. 18724311.8, dated Nov. 6, 2020, 5 pages.

"Opinion of the Scientific Panel on Food Additives, Flavourings, Processing Aids, and Materials in Contact with Food on a Request from the Commission related to Pullulan PI-20 for use as a new food additive," *The EFSA Journal*, vol. 85, pp. 1-32, (Jul. 13, 2004).

Petition for Inter Partes Review of U.S. Pat. No. 6,887,307, filed Jul. 27, 2015, 69 pages.

Petition for Inter Partes Review of U.S. Pat. No. 7,267,718, filed Jul. 27, 2015, 58 pages.

"Pullulan," Official Monographs, USP 32-NF 27, 1330-1331, Dec. 1, 2008.

Seo, H. et al., "Production of high molecular weight pullulan by Aureobasidium pullulans HP-2001 with soybean pomace as nitrogen source," *Bioresource Technology*, 95(3):293-299 (Dec. 2004; published online Apr. 2, 2004).

Tarcha, *Polymers for Controlled Drug Delivery*, CRC Press, p. 55, 1991.

Written Opinion for PCT/IB2012/000176 (dated Aug. 7, 2012), 5 pages.

Xiao, Hong-Su et al., "Phenotypic Plasticity in *Aureobasidium pullans* Isolates," *International Journal of Agriculture& Biology*, 22(1): 167-177 (Jan. 2019).

\* cited by examiner

PULLULAN CAPSULES

CROSS REFERENCE TO RELATED APPLICATIONS

This application is a continuation of U.S. application Ser. No. 16/604,540, filed Oct. 10, 2019, now U.S. Pat. No. 11,576,870, which is the U.S. National Stage of International Application No. PCT/IB2018/000448, filed Apr. 10, 2018, which was published in English under PCT Article 21(2), which in turn claims the benefit of U.S. Provisional Application No. 62/485,854, filed Apr. 14, 2017, each of which is herein incorporated by reference in its entirety.

FIELD

The present application relates to capsules comprising pullulan, to film forming compositions comprising pullulan, and to methods for making capsules.

SUMMARY

Hard and soft capsules comprising pullulan are known. Pullulan provides a number of advantages over other conventional capsule film forming polymers such as gelatin or hydroxypropyl methyl cellulose. Pullulan is a natural product of non-animal origin made without the need for chemical modification. High product quality consistency can be obtained by controlling the fermentation process. The resulting films formed with pullulan have excellent homogeneity and transparency. In addition, such films have very low oxygen permeability. Accordingly, capsules made from pullulan are particularly useful for the filling of oxygen sensitive products such as fish and vegetable oils. Such films and resulting capsules made from pullulan also have relatively low water content, and exhibit high stability over storage, such as with respect to mechanical and dissolution properties.

The natural origin of pullulan and its superior properties as a film forming material has made pullulan a desired polymer for the manufacture of capsules having ingredients of all natural origin. This would enable capsules made with pullulan to meet the requirements for "organic" labeling. Notwithstanding the commercial need for a capsule meeting the organic labeling requirements, no satisfactory pullulan capsules have to date been developed that meet the organic labeling requirements.

In one embodiment, a capsule comprises: pullulan in an amount of at least 70 wt % of the capsule; a setting system in an amount of at least 0.01 wt % of the capsule; and a surfactant comprising a sucroglyceride or a sugar fatty acid ester or mixture thereof. In one embodiment, the surfactant is present in an amount of at least 0.2 wt % of the capsule. The wt % amounts are exclusive of water present in the capsule.

In another embodiment, a capsule consists essentially of: pullulan in an amount of at least 70 wt % of the capsule; a setting system in an amount of at least 0.01 wt % of the capsule; and a surfactant selected from the group consisting of sucroglycerides, sugar fatty acid sugar esters, and mixtures thereof in an amount of at least 0.2 wt % of the capsule. The wt % amounts are exclusive of water present in the capsule.

In another embodiment, the pullulan used to manufacture the capsule is manufactured using an organic fermentation process.

In another embodiment, the sugar fatty acid ester comprises a sugar head group selected from the group consisting of glucose, fructose, galactose, sucrose, maltose, trehalose, lactose, and raffinose.

In another embodiment, the sucroglyceride or the sugar fatty acid ester comprises a lipophilic group derived from the fatty acid esters of a vegetable oil selected from the group consisting of coconut oil, palm oil, palmist oil, soy oil, rapeseed oil, sunflower oil, cottonseed oil, peanut oil, olive oil, canola oil, castor oil, corn oil, flaxseed oil, safflower oil, and sesame oil.

In another embodiment, the surfactant is a sucrose fatty acid ester.

In another embodiment, the surfactant is a sucroglyceride.

In another embodiment, the surfactant is derived from the fatty acids of coconut oil.

In another embodiment, the surfactant is sucrose cocoate.

In another embodiment, the surfactant is present in an amount of from 0.2 wt % to 2 wt % of the capsule composition, or from 0.4 wt % to 1.5 wt % of the capsule composition, or from 0.5 wt % to 1 wt % of the capsule composition (exclusive of water).

In another embodiment, the setting system comprises carrageenan, gellan or agar. In one embodiment, the setting system comprises carrageenan and cations. In another embodiment, the setting system comprises agar and cations.

In one embodiment, the capsules have a $Ca^{2+}$ content of at least 200 mg/kg, or at least 300 mg/kg, or even at least 500 mg/kg.

In one embodiment, the capsules have a $Mg^{2+}$ content of at least 30 mg/kg, or at least 40 mg/kg, or even at least 50 mg/kg.

In one embodiment, the capsules have a ratio of $K^+/(Mg^{2+}+Ca^{2+})$ that is less than 50, or less than 40, or less than 30, or even less than 20. In another embodiment, the capsule further comprises at least one sequestering agent.

In another embodiment, the capsule further comprising plasticizers or/and flavoring agents.

In another embodiment, the capsule further comprises coloring agents in a range from about 0% to 10% based upon the weight of the composition.

In another embodiment, the capsule comprises a coating.

In another embodiment, a caplet is encapsulated in the capsule.

In another embodiment, a method for manufacturing the capsule of claim 1 or 2, comprises:
   a) providing an aqueous dipping composition comprising pullulan, the setting system, and the surfactant;
   b) dipping mold pins in the aqueous dipping composition;
   c) extracting the mold pins from the aqueous dipping composition such that a film is formed over each of the mold pins;
   d) drying the film to form a solid coating on the mold pins;
   e) removing the solid coating from the mold pins to provide capsule shells.

In another embodiment, the mold pins are lubricated with a mixture of lecithin and a vegetable oil.

In another embodiment, the solid coating is lubricated with a mixture of lecithin and a vegetable oil.

In another embodiment, the mold pins are lubricated with a sucroglyceride or sugar fatty acid ester. In another embodiment, the mold pins a lubricated with a mixture of a sucroglyceride and lecithin.

In another embodiment, the lecithin is selected from the group consisting of soybean lecithin, peanut lecithin, cottonseed lecithin, sunflower lecithin, rapeseed lecithin, corn lecithin, and groundnut lecithin. In a preferred embodiment, the lecithin is sunflower lecithin.

In another embodiment, the vegetable oil is selected from the group consisting of coconut oil, palm oil, palmist oil, soy oil, rapeseed oil, sunflower oil, cottonseed oil, peanut oil, olive oil, canola oil, castor oil, corn oil, flaxseed oil, safflower oil, and sesame oil.

In another embodiment, the lubricant comprises a mixture of coconut oil and sunflower lecithin.

It is to be understood that both the foregoing general description and the following detailed description are exemplary and explanatory only and are not restrictive of the claimed subject matter.

DETAILED DESCRIPTION

Definitions

Figure 1:
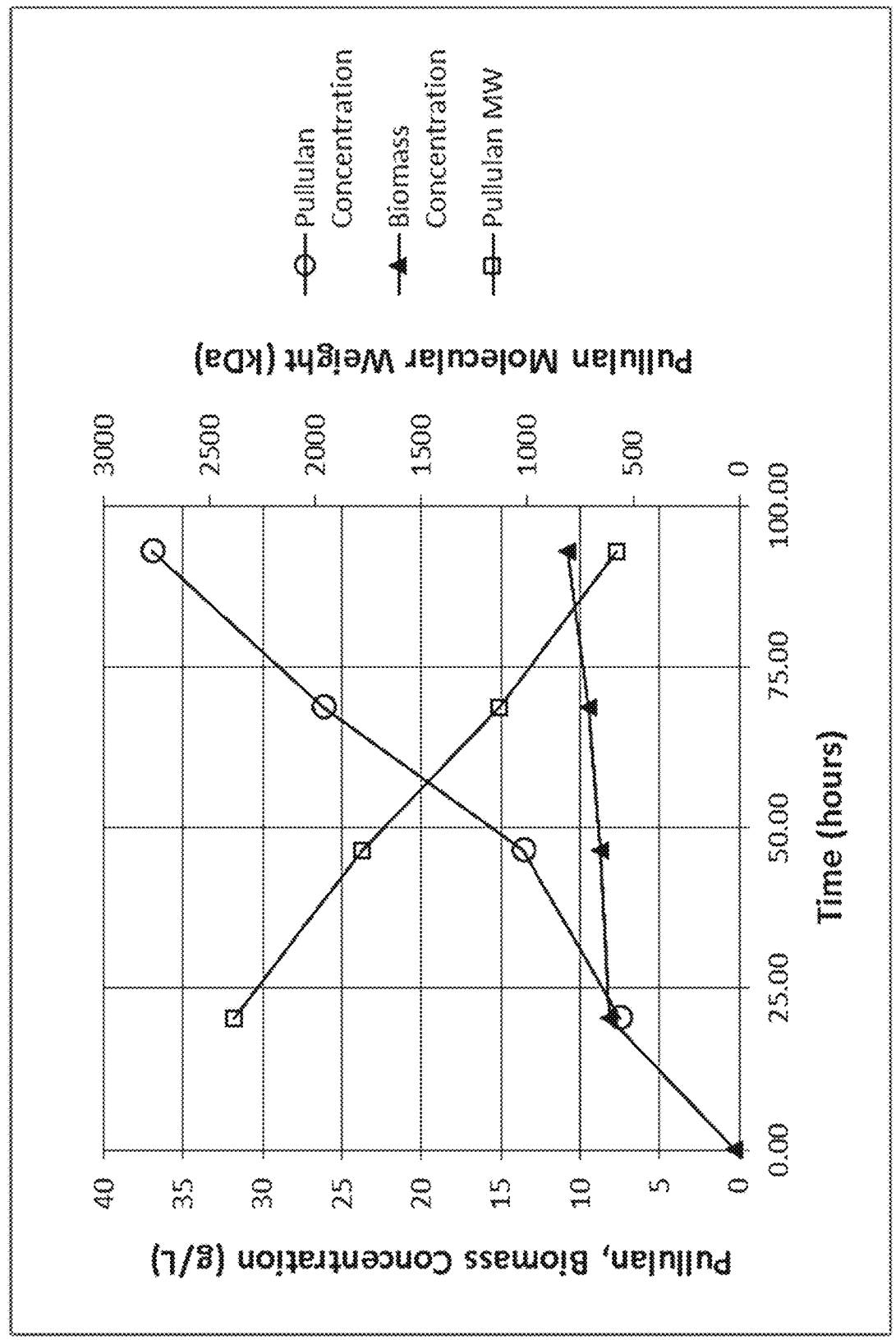
FIG. 1 is a graph of pullulan biomass concentration and pullulan molecular weight versus time.
Figure 2A:
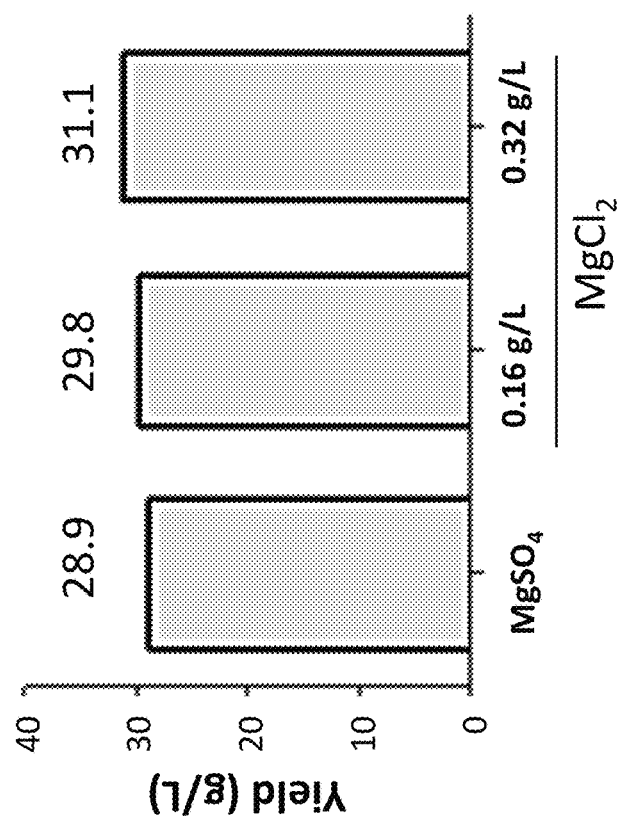
FIGS. 2A and 2B are bar graphs quantifying biomass (FIG. 2A) and yield (FIG. 2B) in the presence of MgSO4, 0.16 g/L MgCl2, or 0.32 g/L MgCl$_2$.
Figure 2B:
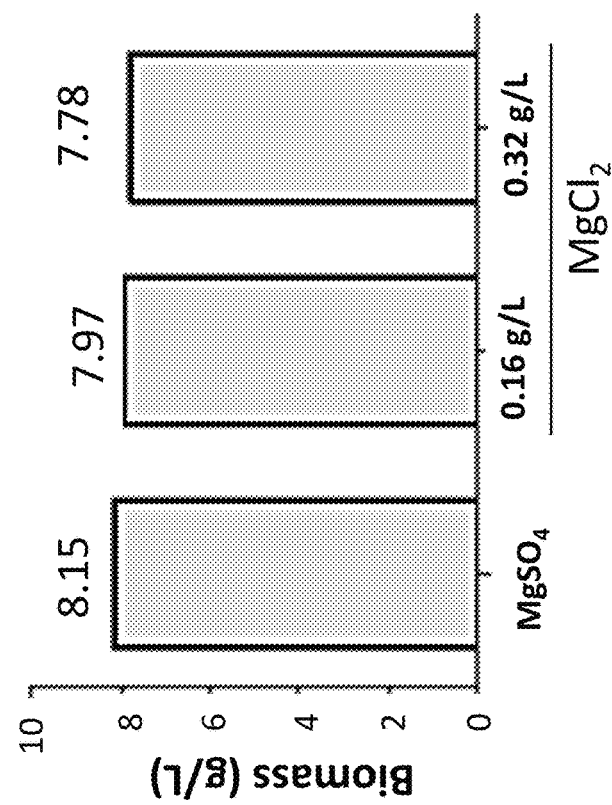

As used herein, reference to an element by the indefinite article "a" or "an" does not exclude the possibility that more than one of the element is present, unless the context clearly requires that there is one and only one of the elements. The indefinite article "a" or "an" thus usually means "at least one." The disclosure of numerical ranges should be understood as referring to each discrete point within the range, inclusive of endpoints, unless otherwise noted. The term "about" as used in the disclosure of numerical ranges indicates that deviation from the stated value is acceptable to the extent that the deviation is the result of measurement variability and/or yields a product of the same or similar properties.

As used herein, "w/w %" and "wt %" means by weight as a percentage of the total weight.

In one aspect, a composition comprises pullulan, a setting system, water and a surfactant system. For example, a composition can contain from 75% to 95% by weight of pullulan, from 0.1% to 15% by weight of the setting system, and from 0.2 wt % to 3 wt % of the surfactant. For capsule compositions, wt % is based on total weight of contents of the capsule exclusive of any water present in the composition.

Pullulan

Pullulan (CAS number 9057-02-7; chemical synonyms 1,4-1,6-α-D-Glucan, 1,6-α-linked maltotriose) is a polysaccharide polymer consisting of maltotriose units. Three glucose units in maltotriose are connected by an α-1,4 glycosidic bond, whereas consecutive maltotriose units are connected to each other by an α-1,6 glycosidic bond. Maltotetraose units consisting of four 1,4-linked glucose molecules also occur, probably randomly, but are generally rare (about 6%). There is also evidence for a rare occurrence of branching points where poly-maltotriosyl side-chains are attached to the main chain by a 1,3-glycosidic bond.

Pullulan is generally produced from starch by the fungus *Aureobasidium pullulans*. Pullulan has good film forming properties and a particularly low oxygen permeability. Its existence was reported for the first time in 1938. Hayashibara Company started the commercial production in 1976.

In one embodiment, the pullulan has low amounts of mono-, di-, and oligosaccharides. Pullulan can be made free of mono-, di-, and oligosaccharides either through a post-manufacturing process step (e.g. precipitation of the mono-, di-, and oligosaccharides from a sample of a commercial pullulan grade in ethanol) or from its very production, by choosing appropriate fermentation conditions.

In one embodiment, the pullulan has an average molecular weight comprised between about 10 kDa to 1,000,000 kDa, preferably between 100 KDa and 750 KDa, more preferably between 200 KDa and 500 KDa. A 10 wt % aqueous solution of pullulan may have a viscosity of from 100 mm$^2$/s to 180 mm$^2$/s at 30° C.

In one embodiment, pullulan is manufactured using an organic fermentation process. In one such process the fermentation media contains calcium phosphate and magnesium chloride. This results in a capsule containing an excess of calcium and magnesium relative to monovalent cations such as potassium. In one embodiment, the capsules have a Ca' content of at least 200 mg/kg, or at least 300 mg/kg, or even at least 500 mg/kg. In another embodiment, the capsules have a Mg' content of at least 30 mg/kg, or at least 40 mg/kg, or even at least 50 mg/kg. In one embodiment, the ratio of $K^+/(Mg^{2+}+Ca^{2+})$ is less than 50, or less than 40, or less than 30, or even less than 20. A process for making pullulan using an organic manufacturing process is disclosed more fully in U.S. provisional patent application No. 62/485,855 filed Apr. 14, 2017, and filed as PCT/US2018/026663, on Apr. 9, 2018, both incorporated in their entireties by reference.

Setting System

The addition of a setting system, preferably based on polysaccharides, to pullulan solutions enables the adaptation of specific and desired gelling properties for the production of hard pullulan capsules by a conventional dipping process. In the dip molding process, the aqueous film forming pullulan solution from which the capsules are made remains on the mold pins after dipping, and does not flow down the pins. Otherwise the obtained film will not have the desired uniform thickness.

In one embodiment the setting system comprises a hydrocolloid or mixtures of hydrocolloids. Suitable hydrocolloids or mixtures thereof may be selected from natural seaweeds, natural seed gums, natural plant exudates, natural fruit extracts, biosynthetic gums, gelatines, and polysaccharides such as starch or cellulose derivatives.

In one embodiment, the polysaccharides are selected from the group comprising alginates, agar gum, guar gum, locust bean gum (carob), carrageenan, tara gum, gum arabic, ghatti gum, *Khaya grandifolia* gum, tragacanth gum, karaya gum, pectin, arabian (araban), xanthan, gellan, starch, Konjac mannan, galactomannan, funoran, and other exocellular polysaccharides. Preferred are exocellular polysaccharides.

Preferred exocellular polysaccharides for use in the present invention are selected from the group comprising xanthan, acetan, gellan, welan, rhamsan, furcelleran, succinoglycan, scleroglycan, schizophyllan, tamarind gum, curdlan, and dextran.

In a further preferred embodiment of the present invention the hydrocolloids of the setting system are kappa-carrageenan or gellan gum or combinations like xanthan with locust bean gum or xanthan with konjac mannan.

In one embodiment, the setting system is kappa-carrageenan with cations. In another embodiment, the setting system is gellan gum with cations. In another embodiment the setting system is agar with cations. These setting systems produce high gel strength at low concentrations and have good compatibility with pullulan.

As mentioned above, the setting system may contain a cation containing salt. The cation containing salt in the setting system serves to enhance the setting ability of the gelling agents. Preferably, the salt comprises cations such as $K^+$, $Li^+$, $Na^+$, $NH_4^+$, $Ca^{2+}$, or $Mg^{2+}$, etc. The amount of cations in the capsule is from 0.01 to 1 wt %, preferably less than 3 wt %.

Surfactant

The pullulan containing compositions further comprise a surfactant that is selected from the group consisting of sucroglycerides, sugar fatty acid esters, and mixtures thereof.

Sucroglycerides are obtained by reacting sucrose with an edible fat or oil with or without the presence of a solvent. They consist of a mixture of mono- and di-esters of sucrose and fatty acids together with mono-, di- and triglycerides from the fat or oil. Exemplary fats and oils include lard oil, tallow, coconut, palm oil, and palmist oil. In one embodiment, the sucroglyceride is selected from the group consisting of coconut oil sucroglyceride, palm oil sucroglyceride, palmist oil sucroglyceride, soy oil sucroglyceride, rapeseed oil sucroglyceride, sunflower oil sucroglyceride, cottonseed oil sucroglyceride, palmist oil sucroglyceride, peanut oil sucroglyceride, olive oil sucroglyceride, canola oil sucroglyceride, castor oil sucroglyceride, corn oil sucroglyceride, flaxseed oil sucroglyceride, safflower oil sucroglyceride, and sesame oil sucroglyceride.

A preferred sucroglyceride is coconut oil sucroglyceride, or sucrose cocoate. Sucrose cocoate is a thick liquid that is pale yellow in color and derived from the fatty acids in coconut oil.

Sugar fatty acid esters are nonionic surfactants consisting of a sugar as the hydrophilic group and a fatty acid as lipophilic group. They are also referred to as sugar esters. In one embodiment, the only surfactants present in the composition are sugar fatty acid esters. Sugar ester fatty acids may be prepared from sugar and methyl and ethyl esters of food fatty acids by esterification in the presence of a catalyst or by extraction from the appropriate glyceride, such as from sucroglycerides.

Exemplary sugars that may be used as the head group include monosaccharides such as glucose, fructose, and galactose, disaccharides such as sucrose, maltose, trehalose and lactose, and trisaccharides such as raffinose.

Exemplary fatty acids that may be used as the lipophilic group include fatty acids having from 6 to 18 carbon atoms, including capyrlic acid (C8), decanoic acid (C10), lauric acid (C12), myristic acid (C14), palmitic acid (C16) and oleic acid (C18). The lipophilic group may be derived from the fatty acid esters from vegetable oils, such as those selected from the group consisting of coconut oil, palm oil, palmist oil, soy oil, rapeseed oil, sunflower oil, cottonseed oil, peanut oil, olive oil, canola oil, castor oil, corn oil, flaxseed oil, safflower oil, and sesame oil.

In a preferred embodiment, the vegetable oil is coconut oil.

In one embodiment, the sugar fatty acid ester is a sucrose fatty acid ester. Such sucrose esters may be formed from combining sucrose with particular fatty acids, and include sucrose laurate, sucrose stearate, sucrose erucate, sucrose oleate, sucrose palmitate, sucrose myristate, sucrose behenate, and sucrose ricenoleate. It is to be understood that such sucrose esters include the mono-, di-, tri- and poly-esters.

In one embodiment, the surfactant may also contain lecithin. The lecithin may be selected from any naturally occurring plant based source. In one embodiment, the lecithin is selected from the group consisting of soybean lecithin, peanut lecithin, cottonseed lecithin, sunflower lecithin, rapeseed lecithin, corn lecithin, and groundnut lecithin. In a preferred embodiment, the lecithin is sunflower lecithin.

The surfactant is present in an amount sufficient to aid in film formation on the mold pins during manufacturing. In one embodiment, the surfactant is present in an amount of at least 0.2 wt % of the capsule composition (exclusive of water content). In one embodiment, the amount of surfactant is present in an amount of from 0.2 wt % to 2 wt % of the capsule composition, or from 0.4 wt % to 1.5 wt % of the capsule composition, or from 0.5 wt % to 1 wt % of the capsule composition (exclusive of water).

Water

The capsules also generally comprise between 2 wt % and 20 wt %, preferably between about 5 wt % and 15 wt % of moisture or water over the total weight of the capsule. Unless otherwise indicated, when discussing capsule compositions, moisture and water are terms that can be used interchangeably. The amount of water present in the capsule compositions depends on both the materials present in the capsule, as well as the relative humidity of the environment in which the capsules are stored. (Accordingly, relative amounts of materials in the capsule compositions is determined relative to compositions not including water, since the amount of water is variable depending on the relative humidity of the environment.)

Typically, a capsule of the invention is dried to water content between about 10 wt % and 15 wt %. However, water content can be brought to lower % by e.g. further drying, capsule shell storage at low relative humidity or filling the capsule with hygroscopic substances.

Optional Materials

In addition to the pullulan, setting system, surfactant and water, the capsule compositions may contain a variety of other materials and processing aids, including those typically used in the manufacture of capsules.

Optionally, the capsule composition may further comprise at least one sequestering agent. Sequestering agents may be selected from the group consisting of ethylenediaminetetraacetic acid, acetic acid, boric acid, citric acid, edetic acid, gluconic acid, lactic acid, phosphoric acid, tartaric acid, or salts thereof, methaphosphates, dihydroxyethylglycine, lecithin or beta cyclodextrin and combinations thereof. Especially preferred is ethylenediaminetetraacetic acid or salts thereof or citric acid or salts thereof.

In the case that gellan is used as gelling agent, the compositions preferably contain a sequestering agent to improve the capsule solubility. The preferred sequestering agents are ethylenediaminetetraacetic acid or salts thereof and citric acid and salts thereof. The amount is preferably less than xwt % in the capsule compositions.

In another embodiment the capsule composition may additionally comprise pharmaceutically or food acceptable coloring agents in the range of from 0.01 wt % to 10 wt %. The coloring agents may be selected from the group consisting of azo-, guinophthalone-, triphenylmethane-, xanthene- or indigoid dyes, iron oxides or hydroxides, titanium dioxide or natural dyes or mixtures thereof. Examples are patent blue V, acid brilliant green BS, red 2G, azorubine, ponceau 4R, amaranth, D+C red 33, D+C red 22, D+C red 26, D+C red 28, D+C yellow 10, yellow 2 G. FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, clorophyllin, canthaxanthin, caramel, or betanin.

In addition, the capsule compositions may optionally further include other minor components such as titanium dioxide and/or colorants such as mineral colorants, natural colorants, and tar colorants, anti-oxidants and the like.

In one embodiment, the pullulan composition optionally comprises one or more pharmaceutically or food acceptable plasticisers. In one embodiment, the one or more plasticizers are selected in the group of plasticizers typically used in the manufacture of hard capsule shells and in particular in the group consisting of: phthalic esters (e.g. dimethyl-, diethyl-, dibutyl-, diisopropyl- and dioctyl-phtalate); citric esters (e.g. triethyl-, tributyl-, acetyltriethyl- and acetyltributyl-citrate); phosphoric esters (e.g. triethyl-, tricresyl, triphenyl-phosphate); oils (e.g. purified mineral oils, ricin oil, corn oil, cotton oil); butyl stearate; dibutyl sebacate; dibutyl tartrate; diisobutyl adipate, glycerol monostearate; glycerol triacetate; tributyrin; oleic acid; stearic acid; cetylic acid; myristic acid; propylene glycol; glycerol; PEG 4000, PEG 6000, and mixtures thereof.

In one embodiment, the aqueous composition of the invention contains one or more pharmaceutically or food acceptable sweeteners and/or flavoring agents. Such sweeteners and flavoring agents are typically present in amounts from 0.01 wt % to 1 wt % of the pullulan composition.

Method for Making Capsules

In one aspect the capsules are manufactured by a conventional dip molding process as normally used in the production of conventional pullulan capsules. Consequently the use of a surfactant system comprising a sucroglyceride or sugar fatty acid ester enables hard pullulan capsules to be produced with the same equipment used for the production of conventional hard pullulan capsules in the same range of process conditions. Furthermore capsules produced from compositions of the present invention have the same dimensional specifications and allow the use of the existing filling machinery and do not require specific and new equipment for the filling process.

Capsules according to the present disclosure are typically made via a dip-molding process. Dip-molding processes for making acid-resistant two-piece hard capsules comprise the steps of:
  a) providing an aqueous dipping composition comprising pullulan, a setting system, and a surfactant that is a sucroglyceride, a sugar fatty acid ester or mixture thereof;
  b) dipping mold pins in the aqueous dipping composition;
  c) extracting the mold pins from the dipping composition such that a film is formed over each of the mold pins;
  d) drying the film to form a solid coating on the mold pins;
  e) optionally applying an external lubricant to the solid coating on the mold pins;
  f) removing the solid coating from the mold pins to provide capsule shells.

Steps (a) to (f) are typically to be performed in the order they are presented.

As described herein, "finished capsule shells" are those capsule shells for which step (f) has been completed.

In step (a) the aqueous dipping composition is prepared by combining water, pullulan, the setting system, and the sugar fatty acid ester. In one embodiment, the aqueous composition of the invention has a total amount of solids typically comprised between about 10% and 55% by weight, preferably between about 15% and 40%, more preferably between 20% and 30% by weight over the total weight of the composition. For amounts of materials in the aqueous dipping composition, wt % is given based on the total weight of the aqueous dipping composition including water.

In one embodiment, the aqueous composition of the invention has a total amount of solids so that the viscosity of the aqueous dipping composition at a temperature comprised between about 50° C. and 70° C. is between about 500 cPs and 5000 cPs, preferably between about 1000 to 3000 cps.

In one embodiment, the concentration of pullulan in the aqueous dipping composition is in a range of 10 to 60 wt %, preferably 10 to 50 wt %, more preferably 15 to 40 wt %, and most preferably 10 to 40 wt %.

The amount of the setting system is preferably in the range of 0.01 to 5% by weight and especially preferred 0.03 to 1.0% in the aqueous dipping composition. The preferred salt concentration in the aqueous dipping concentration is less than 2 wt %.

In another embodiment of the present invention, the amount of the optional sequestering agent is less than 5% by weight, preferably less than 3%, more preferably 0.01% to 3% by weight, even more preferably 0.5% to 2% by weight especially 0.01 to 1% by weight of the aqueous dipping composition.

In addition, the aqueous dipping compositions may optionally further include other minor components such as titanium dioxide and/or colorants such as mineral colorants, natural colorants, and tar colorants, anti-oxidants and the like. In one embodiment, the coloring agents, or mixtures thereof are present in an amount ranging from about 0 to about 5% by weight, e.g., from about 0 to about 2.5% by weight, and from about 0 to about 1.5% by weight over the total weight of the aqueous dipping composition.

In step (b) mold pins are dipped in the aqueous dipping composition. The relative temperatures of the aqueous dipping composition and mold pins are chosen to result in film formation on the mold pins once the mold pins are dipped into the aqueous composition. In this embodiment the aqueous composition at the time the mold pins are dipped is kept at a temperature of from 45° C. to 65° C., preferably from 50° C. to 65° C. The temperature range of the pins is 25-35° C., meaning that this is the mold pin temperature when mold pins are dipped.

In step (c), the mold pins are extracted from the aqueous dipping composition such that a film is formed over each of the mold pins. After being withdrawn from the aqueous dipping composition, the mold pins can be turned from a "top-down" dipping position to a "top-up" drying position according to conventional capsule dip molding processes. In this step the pins are rotated about a horizontal axis of about 180° with respect to the dipping position of step (c).

In step (d), the film on the mold pins is dried. The purpose of the drying step (d) is to reduce the water content (also referred to herein as "moisture") in the capsule shells on the mold pins. In one embodiment, drying occurs at a temperature above the gelling temperature of the aqueous dipping composition so as to obtain molded capsule shells on the pins. The drying step is preferably carried out at a temperature of less than 65° C., preferably less than 60° C., even more preferably from 25° C. to 45° C.

Step (d) is typically carried out for a period of time from 30 to 60 minutes, preferably not exceeding the above identified temperatures. Generally, the water content in the molded capsule shells is reduced from around 80% to around 10 to 15% by weight, based on the total weight of the molded capsule shells (measured at room conditions).

In step (f) the solid coating is removed from the mold pins to provide capsule shells. The solid coating may be removed using any conventional manufacturing technique.

The solid coating in step (e) and the mold pins may be lubricated. In the case of the solid coating, the lubricant enhances gliding of the capsule shells to facilitate filling and closing. With respect to the mold pins, the lubricant facilitates removal of the capsule shells. In yet another aspect of the invention, the lubricant used for the external application to the solid coatings and/or to the mold pins is selected from a mixture of lecithin and a vegetable oil. The lecithin may be selected from any naturally occurring plant based source. In one embodiment, the lecithin is selected from the group consisting of soybean lecithin, peanut lecithin, cottonseed lecithin, sunflower lecithin, rapeseed lecithin, corn lecithin, and groundnut lecithin. In a preferred embodiment, the lecithin is sunflower lecithin.

The vegetable oil may be selected from any naturally occurring vegetable oil. In one embodiment, the vegetable oil is selected from the group consisting of coconut oil, palm oil, palmist oil, soy oil, rapeseed oil, sunflower oil, cottonseed oil, peanut oil, olive oil, canola oil, castor oil, corn oil, flaxseed oil, safflower oil, and sesame oil. In a preferred embodiment, the vegetable oil is coconut oil.

The relative amount of lecithin to vegetable oil ranges from 90/10 lecithin/vegetable oil to 50/50 lecithin/vegetable oil.

In one embodiment, the lubricant comprises a mixture of coconut oil and sunflower lecithin. The mixture of sunflower lecithin and coconut oil is at a ratio of between 90/10 to 50/50 sunflower lecithin/coconut oil, more preferably between 80/20 and 60/40 sunflower lecithin/coconut oil.

In another embodiment, the lubricant comprises a sucroglyceride or sugar fatty acid ester. In one embodiment, the lubricant is a sucroglyceride, preferably sucrose cocoate. In another embodiment, the lubricant comprises a sugar fatty acid ester derived from coconut oil. The lubricant may also optionally comprise lecithin in addition to the sucroglyceride or sugar fatty acid ester in a ratio of from 1/99 to 50/50 lecithin/sucrose glyceride or lecithin/sugar fatty acid ester.

In one embodiment, the lubricant comprises a mixture of sucrose cocoate and sunflower lecithin in a ratio of from 1/99 to 50/50 sunflower lecithin/sucrose cocoate. In one embodiment, the lubricant consists essentially of a mixture of sucrose cocoate and sunflower lecithin in a ratio of from 1/99 to 50/50 sunflower lecithin/sucrose cocoate.

The molded capsule shells mentioned to above, generally refer to both bodies and caps, depending on the shape of the mold pin. Thus, after step (e) the dried capsule shells on the dipping pins can be processed according to conventional steps. This means that in general after step (e), the capsule shells (bodies and caps) are stripped from the pins. This step can be followed by cutting the stripped shells to a desired length.

Methods of Use

The capsule compositions are suitable for use in pharmaceutical, veterinary, food, cosmetic or other products.

Drugs (i.e. medicaments) suitable for use in the capsules described herein may take any form and be for any treatment of a human or animal subject. This includes not only pharmaceutical compounds but also dietary supplements such as vitamins, minerals and the like. The drug may be in a state selected from solid or liquid, preferably solid, at room temperature and atmospheric pressure, and comprises one or more active compounds. The medicament may be solid and in the form of spray dried dispersions, pellets, granules and the like.

Suitable compounds (and generally encompassed by the term "medicament" as used herein) for delivery according to the disclosure include, but are not limited to, particulate, powder, waxy, liquid, and/or pellet forms of the following:

a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, cadobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizol, doxepin, dipotassiumchlorazepat, tetrazepam, estramustinephosphate, terbutaline, captopril, maprotiline, prazosin, atenolol, glibenclamid, cefaclor, etilefrin, cimetidine, theophylline, hydromorphone, ibuprofen, primidone, clobazam, oxaceprol, medroxyprogesterone, flecainide, Mg pyhdoxal-5-phosphateglutaminate, hymechromone, etofyllineclofibrate, vincamine, cinnarizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-aminosalicyclic acid, dihydralazine, magaldrate, phenprocoumon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cinnarizine, clonazepam, codeine, dexamethasone, dicumarol, digoxin, drotaverine, gramicidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbital, phenylbutazone, phenytoin, prednisone, reserpine, spironolactine, streptomycin, sulfamethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), anti-emetics, anticonvulsants, antiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/ metformin, and thiazolidinedione), thyroid hormones, antithyroid drugs, calcitonin, diphosphonate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, diethylstilbestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, oils such as krill oil and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS;

f) probiotics and yeast, such as bacteria selected from the group consisting of *Lactobacillus* (Döderlein's bacilli) such as *Lactobacillus crispatus, Lactobacillus jensinii, Lactobacillus johnsonii, Lactobacillus gasseri, Enterococcus faecium*, or fungi selected from the group of Saccharomycetales such as *Saccharomyces boulardii*.

g) hormones, such as estrogen (i.e. a natural estrogen or a synthetic compound that mimics the physiological effect of natural estrogens) including, without limitation, estradiol (17-estradiol), estridiol acetate, estradiol benzoate, estridiol cypionate, estridiol decanoate, estradiol diacetate, estradiol heptanoate, estradiol valerate, 17a-estradiol, estriol, estriol succinate, estrone, estrone acetate, estrone sulfate, estropipate (piperazine estrone sulfate), ethynylestradiol (17a-ethynylestradiol, ethinylestradiol, ethinyl estradiol, ethynyl estradiol), ethynylestradiol 3-acetate, ethynylestradiol 3-benzoate, mestranol, quinestrol, nitrated estrogen derivatives or combinations thereof; or progestin (i.e. natural or synthetic compounds that possesses progestational activity including, without limitation, nortestosterone, ethynyltestosterone, deacetylnorgestimate, hydroxyprogesterone, 19-norprogesterone, 3P-hydroxydesogestrel, 3-ketodesogestrel (etonogestrel), acetoxypregnenolone, algestone acetophenide, allylestrenol, amgestone, anagestone acetate, chlormadinone, chlormadinone acetate, cyproterone, cyproterone acetate, demegestone, desogestrel, dienogest, dihydrogesterone, dimethisterone, drospirenone, dydrogesterone, ethisterone (pregneninolone, 17a-ethynyltestosterone), ethynodiol diacetate, fluorogestone acetate, gastrinone, gestadene, gestodene, gestonorone, gestrinone, hydroxymethylprogesterone, hydroxymethylprogesterone acetate, hydroxyprogesterone, hydroxyprogesterone acetate, hydroxyprogesterone caproate, levonorgestrel (1-norgestrol), lynestrenol (lynoestrenol), mecirogestone, medrogestone, medroxyprogesterone, medroxyprogesterone acetate, megestrol, megestrol acetate, melengestrol, melengestrol acetate, nestorone, nomegestrol, norelgestromin, norethindrone (norethisterone) (19-nor-17a-ethynyltestosterone), norethindrone acetate (norethisterone acetate), norethynodrel, norgestimate, norgestrel (d-norgestrel and dl-norgestrel), norgestrienone, normethisterone, progesterone, promegestone, quingestanol, tanaproget, tibolone, trimegestone, or combinations thereof.

Once filled, the capsules can be made tamper-proof by using any conventional technique in the field of hard capsules to make the joint permanent. Banding or sealing are suitable techniques. Sealing is a technique well known in the field of hard shell capsules. Various alternative techniques are currently used for this purpose. A suitable procedure is disclosed for example in U.S. Pat. Nos. 4,539,060 and 4,656,066.

In yet another embodiment of the invention, the compositions comprising pullulan, a setting system, water and a sucroglyceride or sugar fatty acid ester may be used to form films. Such films may be used for a variety of other purposes, such as for wrapping food, or for forming aspics or jellies.

It should be understood that the embodiments described herein are not limited thereto. Other embodiments of the present disclosure will be apparent to those skilled in the art from consideration of the specification and practice of the disclosed embodiments. The following examples should be considered as exemplary only, with a true scope and spirit of the present disclosure being indicated by the following claims.

Example 1

Capsules were made as follows. An aqueous dipping solution was prepared by first adding 443 liters of an aqueous solution of pullulan (22 wt % pullulan) to a melt tank and heating the solution to 65° C. 1.65 kg potassium chloride was mixed in 3 liters of 65° C. water, and the resulting solution was added to the melt tank and stirred. 460.5 g of kappa carrageenan (available from CP Kelco, Denmark), was added to the melt tank as follows. An aliquot of 115.13 g of carrageenan was mixed with 3 liters of cold water and then added to the melt tank and stirred. Three additional aliquots of 115.13 g of carrageenan were similarly prepared and added to the melt tank. The solution was then mixed at 50 RPM for 60 minutes, and then placed under vacuum and mixed for an additional 60 minutes. The solution was then mixed for 60 minutes at 33 RPM under vacuum. 160 liters of the solution in the melt tank were then dispensed into a transfer tank. 1600 g of a 12.5 wt % aqueous solution of sucrose cocoate (ESAC 80 available from Tensac, Argentina) was then added to the transfer tank and stirred to form the dipping composition. Water was then added to achieve a viscosity of 800 cps.

Capsules were prepared using dip molding equipment. The aqueous dipping composition was heated to 65° C. The pins were maintained at 30° C.

The mold pins were lubricated with a mixture of sunflower lecithin and coconut oil at a ratio of 70/30 sunflower lecithin/coconut oil.

The resulting capsules had the following composition Excluding Water:

| Ingredient | Wt % |
| --- | --- |
| Pullulan | 97.43 |
| Potassium chloride | 1.61 |
| Kappa Carrageenan | 0.45 |
| Sucrose cocoate | 0.52 |

Including Water:

| Ingredient | Wt % |
| --- | --- |
| Pullulan | 85.73 |
| Potassium chloride | 1.41 |
| Kappa Carrageenan | 0.39 |
| Sucrose cocoate | 0.45 |
| Water | 12.01 |

Example 2

In this example, capsules produced from organic pullulan made according to Example 1 (Capsule A) and Plantcaps® capsules from Capsugel, Greenwood, SC, (Capsule B) were analyzed for $Mg^{2+}$ and $K^+$ content using the standard protocol SM3111B using Flame Atomic Absorption Spectroscopy. In addition, $Ca^{2+}$ content in these capsule was also measured using the standard protocol SM3111D using Flame Atomic Absorption Spectroscopy. Each capsule batch was analyzed in triplicate. From this analysis it was determined that the concentration of both $Mg^{2+}$ and $Ca^{2+}$ is higher in Capsule A than Capsule B. In addition, Capsule A capsules have a lower ratio of monovalent cation ($K^+$) to divalent cations ($Mg^{2+}$ and $Ca^{2+}$).

TABLE 1

Results of Metal Analysis of Capsules

| | Capsule A | | | | Capsule B | | | |
| --- | --- | --- | --- | --- | --- | --- | --- | --- |
| | $Mg^{2+}$ (mg/kg) | $Ca^{2+}$ (mg/kg) | $K^+$ (mg/kg) | $\frac{K+}{(Mg^{2+} + Ca^{2+})}$ | $Mg^{2+}$ (mg/kg) | $Ca^{2+}$ (mg/kg) | $K^+$ (mg/kg) | $\frac{K+}{(Mg^{2+} + Ca^{2+})}$ |
| Replicate 1 | 58.6 | 704 | 7920 | 10.4 | 18.2 | 104 | 7500 | 61.4 |
| Replicate 2 | 58.2 | 680 | 7740 | 10.5 | 18.4 | 101 | 7410 | 62.1 |
| Replicate 3 | 59.4 | 680 | 7590 | 10.3 | 19 | 98.3 | 7560 | 64.5 |
| Mean St. Dev | 58.7 ± 0.6 | 688 ± 13.9 | 7750 ± 165 | 10.4 ± 0.1 | 18.5 ± 0.4 | 101 ± 2.9 | 7490 ± 75 | 62.6 ± 1.6 |

Values expressed in mg metal per kilogram capsule

What is claimed is:

1. A capsule comprising:
   pullulan in an amount of at least 70 wt % of the capsule, wherein the pullulan is manufactured using an organic fermentation process including a fermentation media comprising calcium phosphate and magnesium chloride;
   a setting system in an amount of at least 0.01 wt % of the capsule;
   a surfactant in an amount of greater than 0.2 wt % of the capsule, the surfactant comprising a sucroglyceride or a sugar fatty acid ester or mixture thereof,
   the capsule including
      a $Ca^{2+}$ content of at least 200 mg/kg,
      a $Mg^{2+}$ content of at least 30 mg/kg, and
      $K^+$, with a mass ratio of $K^+/(Mg^{2+}+Ca^{2+})$ of less than 50,
   wherein the wt % amounts are exclusive of water present in the capsule.

2. The capsule of claim 1, wherein:
   (i) the $Ca^{2+}$ content is at least 300 mg/kg; or
   (ii) the $Mg^{2+}$ content is at least 40 mg/kg; or
   (iii) the mass ratio of $K^+/(Mg^{2+}+Ca^{2+})$ is less than 40; or
   (iv) any combination of (i), (ii), and (iii).

3. The capsule of claim 1, wherein the setting system comprises a hydrocolloid.

4. The capsule of claim 3, wherein the hydrocolloid comprises a natural seaweed, a natural seed gum, a natural plant exudate, a natural fruit extract, a biosynthetic gum, a gelatin, a polysaccharide, or any combination thereof.

5. The capsule of claim 1, wherein the setting system comprises kappa carrageenan, gellan gum, agar, xanthan and locust bean gum, or xanthan and konjac mannan.

6. The capsule of claim 1, wherein the sucroglyceride or the sugar fatty acid ester comprises a lipophilic group derived from the fatty acid esters of coconut oil, palm oil, palmist oil, soy oil, rapeseed oil, sunflower oil, cottonseed oil, peanut oil, olive oil, canola oil, castor oil, corn oil, flaxseed oil, safflower oil, sesame oil, or any combination thereof.

7. The capsule of claim 1, wherein the surfactant is a sugar fatty acid ester.

8. The capsule of claim 7, wherein the sugar fatty acid ester comprises a sugar head group selected from glucose, fructose, galactose, sucrose, maltose, trehalose, lactose, and raffinose.

9. The capsule of claim 8, wherein the surfactant is a sucrose fatty acid ester.

10. The capsule of claim 1, wherein the surfactant is a sucroglyceride.

11. The capsule of claim 10, wherein the sucroglyceride is coconut oil sucroglyceride, palm oil sucroglyceride, palmist oil sucroglyceride, soy oil sucroglyceride, rapeseed oil sucroglyceride, sunflower oil sucroglyceride, cottonseed oil sucroglyceride, palmist oil sucroglyceride, peanut oil sucroglyceride, olive oil sucroglyceride, canola oil sucroglyceride, castor oil sucroglyceride, corn oil sucroglyceride, flaxseed oil sucroglyceride, safflower oil sucroglyceride, sesame oil sucroglyceride, or any combination thereof.

12. The capsule of claim 1, wherein the surfactant comprises sucrose cocoate.

13. The capsule of claim 1, wherein the pullulan has an average molecular weight of 10 kDa to 1,000,000 kDa.

14. The capsule of claim 1, wherein the pullulan has an average molecular weight of 100 kDa to 750 kDa.

15. The capsule of claim 1, further comprising a sequestering agent, a plasticizer, a sweetener, a flavoring agent, a coloring agent, or any combination thereof.

16. The capsule of claim 1, further comprising a coating.

17. A caplet encapsulated in a capsule according to claim 1.

18. A method for manufacturing the capsule of claim 1, comprising:
    providing an aqueous dipping composition comprising pullulan, the setting system, the surfactant, $Ca^{2+}$, $Mg^{2+}$, and $K^+$;
    dipping mold pins in the aqueous dipping composition;
    extracting the mold pins from the aqueous dipping composition such that a film is formed over each of the mold pins;
    drying the film to form a solid coating on the mold pins; and
    removing the solid coating from the mold pins to provide capsule shell bodies and caps.

* * * * *